United States Patent [19]
Belau et al.

[11] Patent Number: 5,716,470
[45] Date of Patent: Feb. 10, 1998

[54] LOOP MATERIAL FOR IMPROVED ATTACHMENT TO DISPOSABLE GARMENTS

[75] Inventors: Tom Russell Belau, Hortonville; Mark Michael Mleziva; John Frederick Steffen, both of Appleton, all of Wis.

[73] Assignee: Kimberly-Clark Worldwide, Inc., Neenah, Wis.

[21] Appl. No.: 872,090

[22] Filed: Jun. 10, 1997

Related U.S. Application Data

[63] Continuation of Ser. No. 427,541, Apr. 24, 1995, abandoned.

[51] Int. Cl.$^6$ ............................. A61F 13/62; B05D 3/10
[52] U.S. Cl. ............................. 156/66; 427/154; 427/336; 604/391
[58] Field of Search ............................. 156/66; 427/154, 427/155, 331, 336, 353; 428/99, 100; 604/391

[56] References Cited

U.S. PATENT DOCUMENTS

| | | | |
|---|---|---|---|
| 2,865,783 | 12/1958 | Henderson | 427/353 |
| 4,798,603 | 1/1989 | Meyer et al. | |
| 4,894,060 | 1/1990 | Nestegard | 604/391 |
| 5,176,668 | 1/1993 | Bernardin | |
| 5,176,672 | 1/1993 | Bruemmer et al. | |
| 5,192,606 | 3/1993 | Proxmire et al. | |
| 5,318,555 | 6/1994 | Siebers et al. | |
| 5,476,702 | 12/1995 | Datta | 428/99 |
| 5,482,747 | 1/1996 | Hayes | 427/353 |
| 5,509,915 | 4/1996 | Hanson et al. | 604/378 |
| 5,656,111 | 8/1997 | Dilnik et al. | 156/66 |

FOREIGN PATENT DOCUMENTS

WO95/05140  2/1995  WIPO.

OTHER PUBLICATIONS

"Hackh's Chemical Dictionary" (McGraw–Hill Book Co., 4th ed., 1969), entry for sizing, p. 614.
"Webster's New Collegiate Dictionary" (G. & C. Merriam Co., 1981), entry for lubricant, p. 677.
"Webster's New Collegiate Dictionary" (G. & C. Merriam Co., 1981), entries for sizing (noun) and $^3$size, p. 1078.
Hawley's Condensed Chemical Dictionary, Tenth Ed., Van Nostrand Reinhold Co., (1981), p. 927.

*Primary Examiner*—Daniel Stemmer
*Attorney, Agent, or Firm*—Brinks Hofer Gilson & Lione

[57] ABSTRACT

Disclosed is a process for producing a loop material suitable for use on a disposable garment. The process includes the following steps. Forming a woven loop material having a lubricating material thereon. The lubricating material is present on the woven loop material in an amount effective to assist in the formation of the woven loop material. The woven loop material is rinsed with a liquid to form a rinsed loop material. The rinsing process causes the amount of lubricating material on said woven loop material to be reduced. Finally, the rinsed loop material is attached to the disposable garment. A disposable absorbent garment including the rinsed loop material is also described.

12 Claims, 1 Drawing Sheet

5,716,470

LOOP MATERIAL FOR IMPROVED ATTACHMENT TO DISPOSABLE GARMENTS

This is a continuation of application Ser. No. 08/427,541, filed Apr. 24, 1995, now abandoned.

BACKGROUND OF THE INVENTION

1. Field of the Invention

The present invention relates to a loop material suitable for use on a disposable garment.

2. Description of the Related Art

Mechanical fasteners such as hook-and-loop type fasteners are known for use on disposable garments. Typically, such hook-and-loop fasteners comprise a knitted or woven material having raised loops and a hook material comprising hook or hooklike elements which are capable of engaging with the raised loop material. During the manufacture of such knit or woven materials, processing aids such as lubricating materials are often employed to assist in the manufacturing process. Such lubricating materials are generally applied prior to the actual knitting or weaving process or prior to a separate napping process in which the loops are raised for better engagement with the hook material.

Such loop materials are generally attached to disposable garments through the use of adhesives. The presence of the lubricating materials on the raised loop materials has been found, in some circumstances, to interfere with the adhesion of the loop material to a disposable garment.

In order to overcome this problem, various means have been tried. For example, the problem may be reduced by applying greater levels of adhesive to attach the loop material to the disposable garments. Alternatively, additional materials have been applied to the loop material in an attempt to assist in the adhesion process. Such additional materials are often referred to as tie coat materials which are intended to serve as an interface between the loop material and the adhesive to provide better adhesion than would be achieved by applying the adhesive directly to the loop material. These solutions have not proven entirely acceptable.

SUMMARY OF THE INVENTION

In a first aspect, the present invention is directed to a process for producing a loop material suitable for use as a mechanical fastener component of a disposable garment. The process comprises the following sequential steps.

1. Forming a woven loop material having a lubricating material thereon in an amount effective to assist in the formation of the woven loop material.

2. Rinsing the woven loop material with a liquid to form a rinsed loop material whereby the amount of lubricating material on said woven loop material is reduced.

3. Attaching the rinsed loop material to the disposable garment.

In a second aspect, the present invention relates to a disposable absorbent garment defining a first waist portion, a second waist portion, and an intermediate portion connecting said first and second waist portions. The garment comprises an outer cover, a bodyside liner superposed on said outer cover, and an absorbent core located between the outer cover and the bodyside liner. A rinsed loop material is attached to the outer cover in the first or second waist portion. The disposable absorbent garment further includes a hook material releasably engageable with said rinsed loop material. The hook material is attached to said disposable absorbent garment.

DETAILED DESCRIPTION OF THE PREFERRED EMBODIMENT

Figure 1:
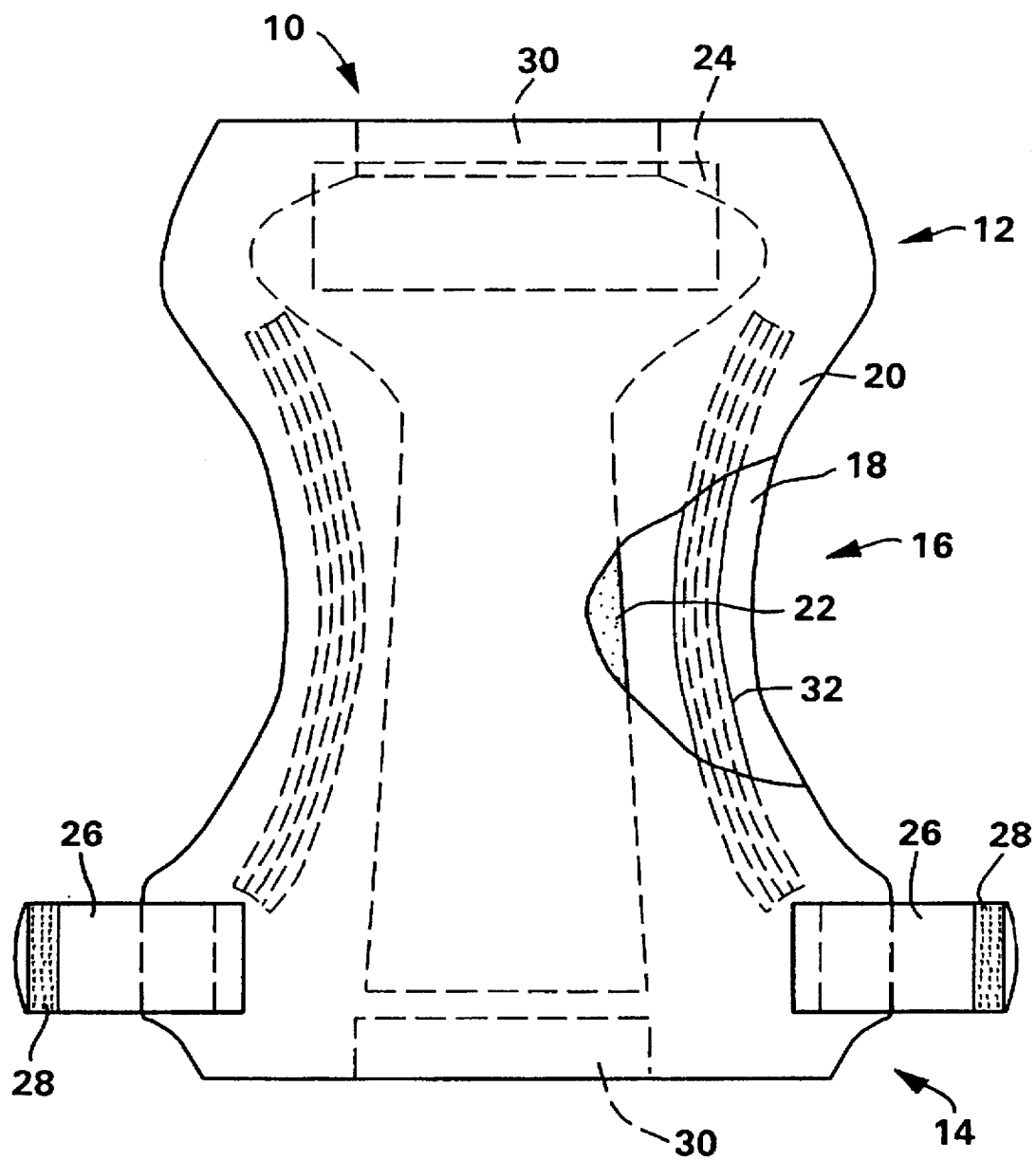
FIG. 1 illustrates a disposable absorbent garment according to the present invention.

In a first aspect, the present invention relates to a process for producing a loop material suitable for use as a mechanical fastener component of a disposable garment. First, a woven loop material is formed having a lubricating material thereon in an amount effective to assist in the formation of the woven loop material. As used herein, reference to a "woven loop material" refers to a material which is woven or knit. Processes for forming such woven loop materials are known to those skilled in the art. Such processes generally involve application of a lubricating material to the fibers from which the woven loop material is formed in order to facilitate fiber handling throughout various production stages, such as warping or knitting. Additionally, lubricating material may be applied to the woven loop material as part of the finishing processes, e.g., napping. The lubricating material serves to assist movement of the yarns, from which the loop material is formed, past one another, without damaging the yarn to an unacceptable degree, and through the processing equipment, without damaging the equipment or yarn to an unacceptable degree.

A wide variety of lubricating materials is known. Such materials include the following: oils, fatty acids, fatty acid esters, fine particulate material, such as silica, and the like. The lubricating materials may be either water soluble or water insoluble. In one preferred embodiment of the present invention, the lubricating material is water soluble.

The presence of the lubricating material has been found to detrimentally affect subsequent attachment of the loop material to the disposable garment. That is, since the lubricating material is often in the form of an oil, fatty acid, fatty acid esters, fine particulate material, such as silica, and the like, such materials often interfere with the bonding between the material from which the yarn is formed and the substrate to which the woven loop material is to be attached. This is particularly true when the woven loop material is to be attached to the disposable garment by an adhesive. However, the lubricating material may also adversely affect other methods of attaching the woven loop material to the disposable garment. The presence of moisture has also been found to aggravate the detrimental effect of the lubricating material.

Applicants have discovered that the detrimental effect associated with the lubricating material, relative to attachment of the woven loop material to the disposable garment, can be reduced by subjecting the woven loop material having a lubricating material thereon to a rinsing process.

Specifically, the woven loop material, having a lubricating material thereon in an amount effective to assist in the formation of the woven loop material, is rinsed with a liquid to form a rinsed loop material. The rinsing process washes some of the lubricating material from the woven loop material whereby the amount of lubricating material on the woven loop material is reduced.

As used herein, reference to a rinsed loop material refers to a woven loop material which has been subjected to a rinsing process whereby the amount of lubricating material present on the woven loop material prior to rinsing is reduced by the rinsing process. As used herein, reference to a rinsing process refers to a process whereby a liquid contacts the woven loop material such that a portion of the lubricating material on said woven loop material is extracted or removed from the woven loop material. Examples of such rinsing processes include washing, spraying, and the like.

When the lubricating material is water soluble, the liquid used in the rinsing step may comprise water. If the lubricating material is not water soluble or otherwise capable of being extracted or removed through the application of water, other liquids, such as polar and nonpolar organic solvents, such as hexane, acetone, methanol, ethanol, carbon tetrachloride, benzene, and the like, may be used. Due to ease of use and cost, water is the preferred liquid for use in the rinsing process. The water may or may not contain additional components, such as surfactants, to assist in the extraction process. Further, the temperature, dwell time, amount of water and method of rinsing has been found to affect the efficiency of the rinsing process.

Processes for producing the woven loop materials often involve weaving or knitting a loop material, napping the loop material to raise the loops off the woven or knitted substrate, and subjecting the napped loop material to a thermosetting process in which the woven loop material may be dimensionally stabilized. The rinsing process can occur either before or after the napping process and either before or after the thermosetting process. In one embodiment of the present invention, the woven loop material is formed from polyester fibers, and rinsing occurs after the napping process but before the thermosetting process. In this manner, the liquid used during the rinsing process can be dried from the surface of the woven loop material during the thermosetting process.

The amount of lubricating material present on the woven loop material after formation of the woven loop material, but before rinsing, is suitably within the range of from about 0.05 to about 5.0, alternatively of from about 0.1 to about 1.0 weight percent based on total weight of the woven loop material and lubricating material. It is desired that the rinsing process remove from about 10 to about 100 percent, alternatively of from about 70 to about 100 percent of the lubricating material from the surface of the woven loop material. Thus, the amount of lubricating material present on the rinsed loop material is suitably from 0 to about 4.5 weight percent, alternatively of from about 0 to about 1.0 weight percent, alternatively of from about 0 to about 0.2 weight percent based on total weight of the rinsed loop material and lubricating material.

Methods for determining the amount of lubricating material on the woven loop material and rinsed loop material are known to those skilled in the art. One such method is described below in connection with the examples.

The rinsed loop material is then attached to the disposable garment. As discussed above, the rinsed loop material may be attached to the disposable garment by any means known to those skilled in the art. The present invention has been found particularly advantageous when the rinsed loop material is to be attached to the disposable garment by an adhesive. Suitable adhesives include pressure-sensitive adhesives, hot melt adhesives, cold melt adhesives, epoxies, water-based adhesives, latex adhesives, and the like. The rinsed loop materials of the present invention can be suitably adhered to a disposable garment by application of a hot melt adhesive such as that commercially available from Findley Adhesives, Inc., Wauwatosa, Wisc., under the trade designation H-2096 or H-2122. The adhesive can be applied in the manner taught in U.S. Pat. No. 5,318,555 issued Jun. 7, 1994, to Siebers et al. in an amount of from about 2 grams per square meter (gsm) to about 10 gsm, alternatively of from about 3 to about 8 gsm. In one embodiment, the rinsed loop is attached to the disposable garment by parallel bars of adhesive. The bars are 0.25 inch wide and are spaced 0.25 inch apart. In the areas in which adhesive is present, the adhesive is present in an amount of about 5.6 gsm.

The woven loop materials tend to be relatively fragile. This is particularly true prior to the thermosetting step generally present in the manufacturing process of such woven loop material. Thus, it is desired to employ a rinsing process which does not deleteriously affect an unacceptable number of the loops present in the woven loop material. By this it is meant that the rinsing process should not destroy, or render inoperative, significant numbers of the loops present in the woven loop material. If too many loops are destroyed or rendered inoperable, the efficiency of the loop material can be severely compromised. Thus, it is desirable that the rinsing process be as gentle as possible on the woven loop material. For this reason, the rinsing process is suitably carried out by spraying or washing (with or without agitation). In one particular embodiment of the present invention, the rinsing process is conducted with water as the rinsing liquid. The water is at a temperature of 170° F., and is applied to the woven loop material by pressurized spraying from the non-loop side of the material. The water is applied in an amount of about 0.2 pound of water to about 1.65 pounds of woven loop material. A suitable range of water to be applied in a spray process is from about 0.2 to about 10.0 pounds water per pound of woven loop material. A suitable range of water to be used in a bath process (woven loop submerged in water) is from about 2.0 to about 25.0 pounds water per pound of nonwoven loop material.

Examples of disposable garments to which the rinsed loop material may be attached includes infant diapers, training pants, feminine care products, adult incontinence products, surgical gowns and drapes, and the like. In one particular embodiment of the present invention, the disposable garment comprises a disposable absorbent garment in the form of an infant diaper. This aspect of the present invention can best be understood by reference to FIG. 1 in which diaper 10 is illustrated. The diaper 10 defines a first waist portion 12, a second waist portion 14, and an intermediate portion 16 connecting said first waist portion 12 and second waist portion 14. The garment comprises an outer cover 18, a bodyside liner 20, and an absorbent core 22 located between the outer cover 18 and the bodyside liner 20. A rinsed loop material 24 is attached to the outer cover 18 in the first waist portion 12. The diaper 10 further includes fastening tabs 26 attached to the diaper 10 in the second waist portion 14. The fastening tabs 26 include a hook material 28 which is releasably engageable with the rinsed loop material 24.

The diaper 10 may further comprise waist elastics 30 and leg elastics 32.

The rinsed loop material of the present invention is suitable for use on a wide variety of disposable absorbent garments. Examples of the disposable absorbent garments on which such rinsed loop materials may be employed can be found in the following U.S. patents and patent applications, all of which are hereby incorporated by reference: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; U.S. patent application Ser. No.

08/096,654 filed Jul. 22, 1993, in the name of Hanson et al., now U.S. Pat. No. 5,509,915; and U.S. patent application Ser. No. 08/263,281 filed Jun. 21, 1994, in the name of Dilnik et al., and now abandoned.

When the rinsed loop material of the present invention is to be attached to a disposable absorbent garment through the use of adhesives, the adhesive add-on necessary to obtain acceptable adhesion can be reduced compared to the amount of adhesive which would be necessary to adhere the woven loop material, prior to rinsing, to the disposable garment. A reduction of from about 10 to about 70 percent is possible. Without intending to be bound hereby, applicants hypothesize that removal of at least a portion of the lubricating material from the woven loop material allows the adhesive to penetrate, to a greater extent, into the loop material fiber matrix. This allows the adhesive to engulf some of the fibers which results in improved adhesion.

As used herein, reference to a "hook material" refers to a material having hook or hooklike projections which are releasably engageable with the rinsed loop material. Such hook material is known to those skilled in the art.

EXAMPLES

Test Methods

Water Extraction

To determine the amount of lubricating material on a woven loop material, the following process is used.

1. 3–4 grams of the material to be tested is provided. The material is weighed to the nearest 0.0001 gram.

2. The sample is placed in a clean 400 milliliter beaker containing several glass boiling beads. 200 milliliters of distilled water is added to the beaker.

3. The beaker is covered with a watch glass and is heated to boiling on a hot plate. The temperature is then reduced and the sample boiled gently for 10 minutes.

4. Using a filter flask under vacuum, the contents of the beaker are filtered through a coarse sintered glass crucible (such as that commercially available from Baxter Scientific under the trade designation catalogue number C8525-1, Pyrex manufacturing number 3294030C. The sample and glass boiling beads are physically transferred to the crucible. Excess water is removed from the sample using vacuum. Twenty milliliters of boiling distilled water is added to the crucible and the sample macerated for 5 seconds with a flattened glass stirring rod. Excess water is then again drawn off under vacuum.

5. The contents of the filter flask are then quantitatively transferred to a 400 milliliter beaker and concentrated to about 30 milliliters by evaporation. Evaporation can occur under air jets while heating on a hot plate or in a forced air oven.

6. The contents of the 400 milliliter beaker are then quantitatively transferred to a 50 milliliter beaker that has been tared to the nearest 0.0001 gram. The tare weight of the beaker is determined by cleaning and drying the beaker, heating briefly (5 minutes) to 105 degrees Celsius, cooling in a desiccator, and weighing.

7. The contents of the beaker are then evaporated to dryness at a temperature below 105 degrees C.

8. Residue in the beaker is then dried at 105 degrees C. for 2 hours, cooled in a desiccator, and weighed to the nearest 0.0001 gram.

The above procedure is then repeated without a test sample being present during the extraction process. The amount of residue present as a result of running distilled water through the above procedure is determined and the extractables (in weight percent) of the test samples determined according to the following formula:

$$\frac{\text{Residue } wt_{TS} - \text{Residue } wt_B}{\text{Sample Weight}} \times 100$$

wherein
Residue $wt_{TS}$=Residue weight of test sample in grams;
Residue $wt_B$=Residue weight of blank in grams; and
Sample weight is in grams.

Wet Adhesion Test

This test is designed to determine the efficiency of an adhesive bond formed between a woven loop material and a nonwoven/film laminate.

A 2.25×6.5–8.0 inch sample of the woven loop material to be tested is provided. The woven loop material is attached to a nonwoven/film laminate material formed from a 24 gsm polypropylene nonwoven material and a 14.6 gsm catalloy-based monolayer film, such as that commercially available from Edison Plastics Company, Newport News, Va., under the trade designation NFST/P-1500. The nonwoven material and the film are thermally bonded together. The nonwoven/film laminate is that commercially used on the HUGGIES® Supreme diaper product, commercially available from Kimberly-Clark Corporation.

The woven loop material to be tested is attached to the nonwoven/film laminate by applying 0.25 inch wide strips of adhesive spaced 0.25 inch apart across the nonloop side of the woven loop material. The adhesive is suitably applied by slot coating. The stripes of adhesive run parallel to the short sides of the loop panel. The adhesive used is a hot melt adhesive commercially available from Findley Adhesives, Wauwatosa, Wisc., under the trade designation H-2096. The adhesive is applied at a temperature of about 330° F. After application of the woven loop material to the nonwoven/film substrate, the woven loop material and nonwoven/film substrate are passed through a nip roll at a pressure of about 40–55 pounds per square inch.

The nonwoven/film laminate is then delaminated by carefully pulling the spunbond material off the film. The woven loop material remains attached to the spunbond material. The woven loop material attached to the spunbond material is then submerged in room temperature tap water with the loop patch down. The nonwoven loop material/spunbond laminate is allowed to remain in the water for 10 seconds. After 10 seconds, the nonwoven loop/spunbond laminate is removed from the water and allowed to drip for about 5 seconds. Starting with one of the corners of the woven loop material, an attempt is made to remove the woven loop material patch from the spunbond material without ripping the spunbond material. If the spunbond material rips at one of the corners, an attempt is made to remove the woven loop patch material along one of the long sides of the patch in an area where there is no adhesive (between the adhesive stripes). If the loop patch cannot be removed from the spunbond without ripping the spunbond, it is said to pass this test. If at least a 2 inch area of the loop patch can be detached from the spunbond without tearing the spunbond, the sample is said to have failed this test. Codes which initially passed the test after a 10 second submersion are then resubmerged in room temperature tap water for an additional 10 minutes. The woven loop/spunbond laminate is then fetested in the manner described above to determine if a 2 inch area of the loop patch can be detached from the spunbond material.

Example 1

Various samples of a woven loop material were obtained from Guilford Mills Inc., Greensboro, N.C. With the exception of the control samples, the woven loop materials had been subjected to a rinsing process according to the present invention. The exact conditions and method of rinsing may have varied from sample to sample. Moreover, the types and amounts of lubricating materials applied to the samples may have varied from sample to sample.

The loop materials thus obtained were adhered to a film/nonwoven laminate such as that described in the Wet Adhesion test and commercially used as the outer cover of the HUGGIES® Supreme Diaper commercially available from Kimberly-Clark Corporation. The loop material was in the form of a patch having the dimensions of 2.25 inches by 6.5–8.0 inches. The film nonwoven laminate has dimensions which are at least 2 inches greater in both the length and width directions. The loop material was applied to the film nonwoven laminate by applying an adhesive, commercially available from Findley Adhesives under the trade designation H-2096, in a series of parallel bars having a width of ¼ inch, spaced ¼ inch apart, and running parallel to the short sides (2.25 inches) of the loop material. The adhesive was applied at 325 degrees F. at an add-on of 5.9 grams per square meter (calculated in the areas of adhesive application ignoring those areas not containing adhesive). The loop material was adhered to the film nonwoven laminate by passing through a nip roll at a pressure of about 40–55 pounds per square inch. The materials thus formed were subjected to the Wet Adhesion test described above, and the results are set forth in Table 1.

As can be seen from Table 1, the rinsing process according to the present invention reduces the amount of lubricating material otherwise present on the loop material. Adhesion of the loop material to the nonwoven film laminate is improved by the process of the present invention. This, in turn, allows for the use of a lower amount of adhesive add-on while still achieving acceptable performance.

Example 2

Two samples of a woven loop material were obtained from Guilford Mills Inc. Each of the samples were formed from polyester fibers and have various lubricating materials present thereon. Additionally, each of the loop material samples were subjected to treatment with an aqueous solution containing 4 weight percent polyvinyl acetate. A portion of each of the samples was subjected to the water extraction test described above to determine the amount of extractables for each test sample. Sample 1 was found to have an extractables level of 0.23 weight percent, and sample 2 was found to have an extractables level of 0.38 weight percent.

Portions of samples 1 and 2 were then subjected to a rinsing procedure. In each case, the sample tested was submerged in an aqueous solution which may, optionally, have contained a surfactant and/or methanol. Further, the sample, while present in the aqueous material, may have been subjected to agitation by reciprocating the wash container. The samples were allowed to remain in the aqueous solution for 2 minutes or 10 minutes. The temperature of the aqueous solution, time in the aqueous solution, and presence or absence of surfactant, methanol, and agitation were varied to determine the effect of these variables on the amount of lubricating material extracted from the woven loop materials. The results of this testing are set forth in Table 2.

TABLE 1

| Loop Material Lot # | Adhesive Add-On[2] | Extractables[3] | Wet Adhesion[4] 10 Sec. | Wet Adhesion[4] 10 Min. |
|---|---|---|---|---|
| 328438 1L6 | 5.9 | 0.14 | P | P |
| 328438 1L3 | 5.9 | 0.14 | P | P |
| 328438 1L5 | 5.9 | 0.12 | P | P |
| 328438 1L7 | 5.9 | 0.11 | P | P |
| 3280943R5 | 5.9 | Not Measured | F | — |
| 3280943R3 | 5.9 | Not Measured | F | — |
| 326330 | 5.9 | 0.03 | P | P |
| 326395[1] | 5.9 | Not Measured | F | — |
| 326395[1] | 4.425 | Not Measured | F | — |
| 328438 1L6 | 2.95 | Not Measured | P | P |
| 328438 1L3 | 4.425 | 0.14 | P | P |
| 328438 1L5 | 4.425 | 0.14 | P | P |
| 328438 1L7 | 4.425 | 0.12 | P | P |
| 326330 | 4.425 | 0.11 | P | P |
| 328438 1L6 | 4.425 | 0.03 | P | P |
| 121672 | 5.9 | 0.15 | P | P |
| 121680 | 5.9 | 0.14 | P | P |
| 3280943L6 | 5.9 | 0.17 | F | — |

[1]Control, not subjected to a rinsing process according to the present invention. Coated with a 4 weight percent aqueous solution of polyvinyl acetate as a tie coat.
[2]In grams per square meter.
[3]In weight percent.
[4]Wet Adhesion Test; P = pass; F = fail

TABLE 2

| | | | Rinse Variables | | | | | | |
|---|---|---|---|---|---|---|---|---|---|
| Run No. | Sample No. | Surfactant[1] | Temp (°F.) | Methanol[2] | Time[3] | Agitation | Initial Ext. | Extracted[4] | % Removal |
| 1 | 2 | 0 | 70 | 0 | 2 | Yes | 0.38 | 0.09 | 76.3 |
| 2 | 2 | 0.1 | 150 | 0 | 2 | No | 0.38 | 0.05 | 86.8 |
| 3 | 1 | 0.1 | 70 | 0 | 10 | Yes | 0.23 | 0.11 | 52.2 |
| 4 | 2 | 0 | 150 | 5 | 2 | Yes | 0.38 | 0.04 | 89.5 |

TABLE 2-continued

| | | | Rinse Variables | | | | | | |
|---|---|---|---|---|---|---|---|---|---|
| Run No. | Sample No. | Surfactant[1] | Temp (°F.) | Methanol[2] | Time[3] | Agitation | Initial Ext. | Extracted[4] | % Removal |
| 5 | 1 | 0 | 70 | 0 | 2 | No | 0.23 | 0.10 | 56.5 |
| 6 | 1 | 0.1 | 150 | 5 | 2 | No | 0.23 | 0.04 | 82.6 |
| 7 | 1 | 0 | 150 | 5 | 10 | Yes | 0.23 | 0.03 | 87.0 |
| 8 | 2 | 0.1 | 70 | 5 | 10 | No | 0.38 | 0.04 | 89.5 |
| 9 | 1 | 0 | 150 | 0 | 10 | No | 0.23 | 0.04 | 82.6 |
| 10 | 1 | 0.1 | 70 | 5 | 2 | Yes | 0.23 | 0.06 | 73.6 |
| 11 | 2 | 0 | 70 | 5 | 10 | No | 0.38 | 0.09 | 76.3 |
| 12 | 2 | 0.1 | 150 | 0 | 10 | Yes | 0.38 | 0.05 | 86.8 |

[1]Weight percent in aqueous solution
[2]Weight percent in aqueous solution
[3]In minutes
[4]Amount extracted by water extraction method after being subjected to the described washing procedure The amount of water or water solution employed during the washing process is equal to about 13.2 pounds of water or solution per pound of nonwoven loop material.

As can be seen from Table 2, the temperature of the wash solution appeared to be the most significant variable tested.

Example 3

Seven woven loop materials were obtained from Guilford Mills, Inc. The woven loop materials had been subjected to different manufacturing conditions, lubricating material treatments, and rinsing treatments. Portions of the samples were weighed and then subjected to a six hour solute extraction with distilled water. The extracts were decanted into beakers and subjected to partial evaporation in a 60° C. oven to reduce the liquid volume. The concentrated extractions were transferred to rated beakers and dried at 60° C. A blank was run, and the percent extractables was calculated as described in the water extraction test described above. The woven loop samples were then subjected to the wet adhesion test described above. The lot numbers, extractables, and test results are set forth in Table 3.

TABLE 3

| Lot # | Extractables (%) | Wet Adhesion 10 sec | Wet Adhesion 10 min |
|---|---|---|---|
| 130 590088-1L | 0.13 | F | — |
| 134 590084-1L | 0.02 | P | P |
| 132 590087-1L | 0.07 | F | — |
| 137 141392-1L | 0.27 | F | — |
| 133 141393-1L | 0.15 | F | — |
| 131 141391-1L | <0.01 | P | P |

As can be seen from Table 3, low extractables levels result in better wet adhesion.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A process for producing a loop material and using said loop material as a mechanical fastener component of a disposable garment, the process comprising the following sequential steps:

forming a woven or knitted loop material having a lubricating material thereon in an amount effective to assist in the formation of said woven or knitted loop material;

rinsing said woven or knitted loop material with a liquid to form a rinsed loop material wherein the amount &lubricating material present on said woven or knitted loop material is reduced; and attaching said rinsed loop material, which has a reduced amount of lubricating material present thereon, to said disposable garment.

2. The process according to claim 1 wherein said lubricating material is selected from the group consisting of oils, fatty acids, and fatty acid esters.

3. The process according to claim 1 wherein said lubricating material is water soluble, and said liquid is water.

4. The process according to claim 1 wherein said lubricating material is present on said woven or knitted loop material, prior to rinsing, in an amount of from about 0.05 to about 5.0 weight percent based on the total weight of said woven or knitted loop material and said lubricating material.

5. The process according to claim 1 wherein rinsing said woven or knitted loop material with a liquid removes from about 10 to about 100 weight percent of the lubricating material on said woven or knitted loop material.

6. The process according to claim 1 wherein rinsing said woven or knitted loop material with a liquid removes from about 70 to about 100 weight percent of the lubricating material on said woven or knitted loop material.

7. The process according to claim 1 wherein said rinsed loop material has from 0 to about 4.5 weight percent of said lubricating material, based on the total weight of the rinsed loop material and the lubricating material, thereon.

8. The process according to claim 1 wherein said rinsed loop material has from about 0 to about 1.0 weight percent of said lubricating material, based on the total weight of the rinsed loop material and the lubricating material, thereon.

9. The process according to claim 1 wherein said disposable garment is a disposable absorbent garment.

10. The process according to claim 1 wherein said rinsed loop material is attached to said disposable garment with an adhesive.

11. The process according to claim 1 wherein said lubricating material is a fine, particulate, water-insoluble material.

12. The process according to claim 1 wherein said lubricating material is a fatty acid or fatty acid ester.

* * * * *

UNITED STATES PATENT AND TRADEMARK OFFICE
CERTIFICATE OF CORRECTION

PATENT NO. : 5,716,470
DATED : February 10, 1998
INVENTOR(S) : Tom R. Belau et al.

It is certified that error appears in the above-identified patent and that said Letters Patent is hereby corrected as shown below:

In column 5, line 42, please replace "3294030C." with --3294030C).--.

In claim 1, line 10, please change "&" to --of--.

Signed and Sealed this

First Day of May, 2001

Attest:

NICHOLAS P. GODICI

Attesting Officer        Acting Director of the United States Patent and Trademark Office